(12) United States Patent
Plascencia et al.

(10) Patent No.: US 11,233,369 B2
(45) Date of Patent: Jan. 25, 2022

(54) POSITIONING CARTRIDGE FOR ELECTRODE

(71) Applicant: Biosense Webster (Israel) Ltd., Yokneam (IL)

(72) Inventors: Rogelio Plascencia, Rancho Cucamonga, CA (US); Patrick Kiernan, Pasadena, CA (US); Steven Campbell, Corona, CA (US); Federico Valdovinos, Whittier, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 452 days.

(21) Appl. No.: 15/913,519

(22) Filed: Mar. 6, 2018

(65) Prior Publication Data

US 2019/0280445 A1  Sep. 12, 2019

(51) Int. Cl.
*H01R 43/20* (2006.01)
*A61B 18/14* (2006.01)
(Continued)

(52) U.S. Cl.
CPC ......... *H01R 43/20* (2013.01); *A61B 18/1492* (2013.01); *A61B 2017/00526* (2013.01);
(Continued)

(58) Field of Classification Search
CPC ................... H01R 43/16; H01R 43/20; A61B 2017/00526; A61B 18/1492; A61B 18/00577; E04C 5/20
See application file for complete search history.

(56) References Cited

U.S. PATENT DOCUMENTS

| 3,043,902 A | * | 7/1962 | Klein | ............... H02G 7/12 174/146 |
| 4,039,778 A | | 8/1977 | Williams | |

(Continued)

FOREIGN PATENT DOCUMENTS

| GB | 2459772 | | 11/2009 |
| GB | 2459772 A | * | 11/2009 |
| WO | 96/05768 | | 2/1996 |

OTHER PUBLICATIONS

Paul Lukas, "A Large Pepperoni, and Don't Skimp on the Cheese", Feb. 1, 2013, pp. 1-5 of 22, https://uni-watch.com/2013/02/01/a-close-look-at-the-little-doohickey-in-the-center-of-a-delivery-pizza/ (Year: 2013).*

(Continued)

*Primary Examiner* — Livius R. Cazan
(74) *Attorney, Agent, or Firm* — Dergosits & Noah LLP; Todd A. Noah

(57) ABSTRACT

A positioning cartridge is disclosed for use during manufacture of an electrode. The positioning cartridge may have a plurality of positioning inserts, each with proximal and distal ends, and a scaffold secured to the proximal ends of each positioning insert. The scaffold may be configured to place the positioning inserts in a defined orientation with respect to each other that corresponds to a plurality of longitudinal bores of the electrode. An electrode may be manufactured using the positioning cartridge. The positioning cartridge may have a plurality of components, such that at least one component is associated with each positioning insert. The plurality of components may be temperature sensors. The positioning cartridge may be configured to position each temperature sensor at a location adjacent an outer surface of the electrode.

13 Claims, 6 Drawing Sheets

(51) Int. Cl.
*A61B 17/00* (2006.01)
*A61B 18/00* (2006.01)

(52) U.S. Cl.
CPC .............. *A61B 2018/00023* (2013.01); *A61B 2018/00351* (2013.01); *A61B 2018/00577* (2013.01); *A61B 2018/00797* (2013.01); *A61B 2018/00821* (2013.01); *A61M 2207/10* (2013.01)

(56) References Cited

U.S. PATENT DOCUMENTS

| | | | |
|---|---|---|---|
| 4,066,320 A * | 1/1978 | Goodrich | H01R 4/2429 439/392 |
| 5,391,199 A | 2/1995 | Ben-Haim | |
| 6,158,886 A | 12/2000 | Dutcher et al. | |
| 6,239,724 B1 | 5/2001 | Doron et al. | |
| 6,332,089 B1 | 12/2001 | Acker et al. | |
| 6,468,260 B1 | 10/2002 | Bumbalough et al. | |
| 6,484,118 B1 | 11/2002 | Govari | |
| 6,500,167 B1 | 12/2002 | Webster, Jr. | |
| 6,522,933 B2 | 2/2003 | Nguyen | |
| 6,618,612 B1 | 9/2003 | Acker et al. | |
| 6,690,963 B2 | 2/2004 | Ben-Haim et al. | |
| 7,729,742 B2 | 6/2010 | Govari | |
| 8,437,832 B2 | 5/2013 | Govari et al. | |
| 8,617,087 B2 | 12/2013 | Schultz | |
| 9,373,881 B2 * | 6/2016 | Thompson, Jr. | H01Q 21/061 |
| 9,675,411 B2 | 6/2017 | Govari et al. | |
| 2002/0095152 A1 | 7/2002 | Ciarrocca et al. | |
| 2003/0231698 A1 | 12/2003 | Yamaguchi et al. | |
| 2004/0068178 A1 | 4/2004 | Govari | |
| 2011/0130648 A1 | 6/2011 | Beeckler et al. | |

OTHER PUBLICATIONS

Extended European Search Report for European Patent Application No. 19160743.1, dated Jul. 3, 2019.

* cited by examiner

POSITIONING CARTRIDGE FOR ELECTRODE

FIELD OF THE PRESENT DISCLOSURE

This disclosure relates generally to methods and devices for percutaneous medical treatment, and specifically to catheters that have temperature sensing capabilities, such as ablation catheters. More particularly, this disclosure relates to a cartridge for use during manufacture of an electrode to reliably position a plurality of thermocouples or other components.

BACKGROUND

Radiofrequency (RF) electrode catheters have been in common use in medical practice for many years. They are used to stimulate and map electrical activity in the heart and to ablate sites of aberrant electrical activity. Specifically, targeted ablation may be performed for a number of indications. For example, ablation of myocardial tissue is well known as a treatment for cardiac arrhythmias by using a catheter to apply RF energy and create a lesion to break arrhythmogenic current paths in the cardiac tissue. As another example, a renal ablation procedure may involve the insertion of a catheter having an electrode at its distal end into a renal artery in order to complete a circumferential lesion in the artery in order to denervate the artery for the treatment of hypertension.

In such procedures, a reference electrode is typically provided and may be attached to the skin of the patient or by means of a second catheter. RF current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the target tissue resulting in formation of a lesion which is electrically non-conductive. The lesion may be formed in tissue contacting the electrode or in adjacent tissue. During this process, heating of the electrode also occurs as a result of conduction from the heated tissue to the electrode itself. As will be appreciated, it is desirable to employ catheters that can sense temperature to help guide the procedure, such as by offering an indication when an efficient ablation temperature has been reached or by reducing conditions under which tissue may be overheated. It is further desirable to provide such electrodes with the ability to sense temperature at multiple locations to more accurately monitor and control the procedure. Accordingly, the temperature sensing elements should be placed accurately and reproducibly within the electrode to maintain consistency among each manufactured electrode.

When the electrode reaches critical temperatures, denaturation of blood proteins causes coagulum formation. Impedance can then rise and limit current delivery. Within tissue, overheating can cause steam bubble formation (steam "pops") with risk of uncontrolled tissue destruction or undesirable perforation of bodily structures. To help mitigate overheating, ablation catheters may be irrigated. For example, Biosense Webster Inc. (Diamond Bar, Calif.) offers the ThermoCool® irrigated-tip catheter for use with its CARTO® integrated mapping and ablation system. The metal catheter tip, which is energized with radio-frequency (RF) electrical current to ablate the tissue, has a number of peripheral holes, distributed circumferentially around the tip, for irrigation of the treatment site. A pump coupled to the catheter delivers saline solution to the catheter tip, and the solution flows out through the holes during the procedure in order to cool the catheter tip and the tissue. Representative details concerning irrigated ablation catheters may be found in commonly-owned U.S. Pat. No. 9,675,411, whose disclosure is incorporated herein by reference in its entirety. Although ablation catheters may be irrigated to provide greater control over the temperature of catheter components and the surrounding tissue, it is still important to accurately monitor temperature at multiple locations. Indeed, the flow of irrigation fluid may be tailored in part based on feedback from the temperature sensors.

While ablation catheters have been discussed as being a representative example, one of ordinary skill in the art will recognize that many types of intravascular devices may benefit from improved temperature sensing capabilities, particularly with regard to techniques help ensure consistent and reproducible placement during manufacture. Accordingly, it would be desirable to provide a cartridge to position multiple temperature sensing elements within an electrode accurately and reliably. As will be described in the following materials, this disclosure satisfies these and other needs.

SUMMARY

The present disclosure is directed to a positioning cartridge for use during manufacture of an electrode. The positioning cartridge may have a plurality of positioning inserts, each with proximal and distal ends, and a scaffold secured to the proximal ends of each positioning insert. The scaffold may be configured to place the positioning inserts in a defined orientation with respect to each other that corresponds to a plurality of longitudinal bores of the electrode.

In one aspect, the scaffold may have at least one arm.

In one aspect, the positioning cartridge may have two positioning inserts and the at least one arm may be secured to each positioning insert.

In one aspect, the scaffold may have at least one arm and each arm may be secured to at least one of the positioning inserts. Further, each arm may be secured to at least two of the positioning inserts.

In one aspect, each positioning insert may have a longitudinal slot. Each longitudinal slot may have a distal stop. Each longitudinal slot may be located at an outermost radius of the positioning cartridge.

In one aspect, the positioning cartridge may include at least one component disposed within each longitudinal slot. The at least one component may be at least one temperature sensor. Additionally, at least two temperature sensors may be disposed within each longitudinal slot.

In one aspect, the positioning cartridge may be deployed within the electrode. Each positioning insert may have at least one associated temperature sensor.

In one aspect, the positioning cartridge may be molded as a monolithic element.

In one aspect, the scaffold further may have a frangible junction adjacent each of the positioning inserts.

This disclosure is also directed to a method for manufacturing an electrode. The method may include providing the electrode, such that the electrode has a plurality of longitudinal bores, providing a positioning cartridge having a plurality of positioning inserts secured by a scaffold configured to place each positioning insert in a defined orientation with respect to each other that corresponds to the longitudinal bores of the electrode, deploying the positioning cartridge within the electrode so that each positioning insert is disposed within each longitudinal bore and removing the scaffold while leaving each positioning insert is disposed within each longitudinal bore.

In one aspect, the positioning cartridge may have a plurality of components, such that at least one component is associated with each positioning insert. The plurality of components may be temperature sensors. The positioning cartridge may be configured to position each temperature sensor at a location adjacent an outer surface of the electrode.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Figure 1:
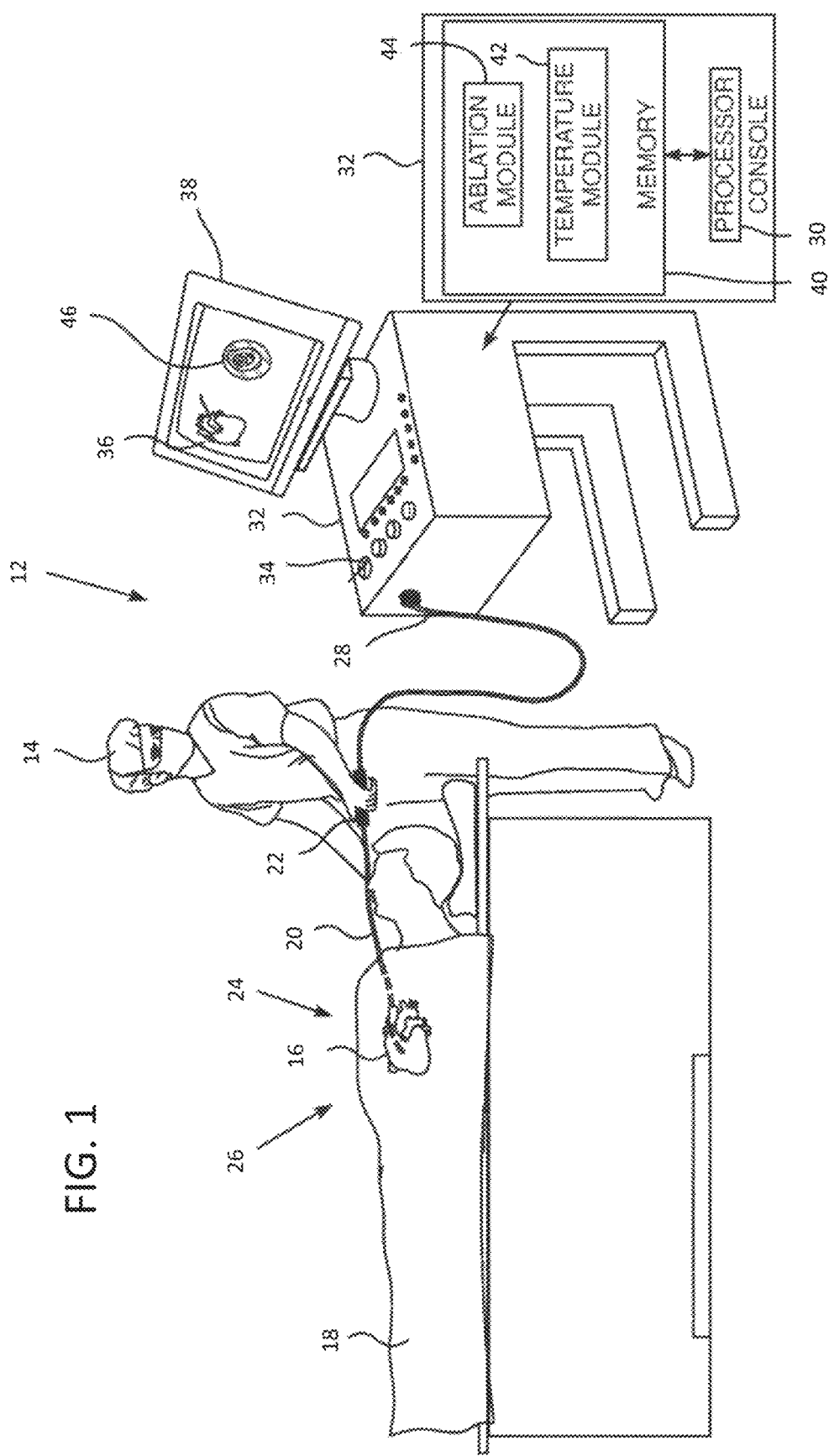
FIG. 1 is a schematic view of an ablation system in accordance with an embodiment of the present invention.

FIG. 1 is a schematic illustration of an invasive medical procedure using system 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it will be understood that embodiments of the present invention are not just applicable to this specific procedure, and may include substantially any procedure on biological tissue or on non-biological material.

In order to perform the ablation, professional 14 inserts a catheter 20 into a lumen of the patient, using handle 22, so that a distal end 24 of the catheter enters the heart of the patient. Distal end 24 comprises at least a tip electrode 26 for contacting locations of the myocardium. Catheter 20 has a proximal end 28 for connection to associated equipment as described below. Distal end 24 of the catheter is described in more detail with reference to FIGS. 3A, 3B and 3C.

System 12 is controlled by a system processor 30, which is located in an operating console 32 of the system. Console 32 comprises controls 34 which are used by professional 14 to communicate with the processor. During the procedure, processor 30 typically tracks a location and an orientation of distal end 24 of the catheter, using any method known in the art. For example, processor 30 may use a magnetic tracking method, wherein magnetic transmitters external to patient 18 generate signals in coils positioned in the distal end. The CARTO® system referenced above uses such a tracking method and additional details may be found in U.S. Pat. Nos. 5,391,199, 6,690,963, 6,484,118, 6,239,724, 6,618,612, 6,332,089, 7,729,742, in PCT Patent Publication WO 96/05768, and in U.S. Patent Publication No. 2004/0068178 A1, whose disclosures are all incorporated herein by reference.

The software for processor 30 may be downloaded to the processor in electronic form, over a network, for example. Alternatively or additionally, the software may be provided on non-transitory tangible media, such as optical, magnetic, or electronic storage media. The track of distal end 24 is typically displayed on a three-dimensional representation 36 of the heart 16 of patient 18 on a screen 38. In order to operate system 12, processor 30 communicates with a memory 40, which has a number of modules used by the processor to operate the apparatus. Thus, memory 40 comprises a temperature module 42 and an ablation module 44, for example, and typically comprises other modules, such as a force module for measuring the force on end 24, a tracking module for operating the tracking method used by processor 30, and an irrigation module allowing the processor to control irrigation provided for distal end 24. For simplicity, such other modules, which may comprise hardware as well as software elements, are not illustrated in FIG. 1. Processor 30 typically uses results of measurements of temperature acquired by module 42 to display on screen 38 a temperature distribution map 46.

Figure 2:
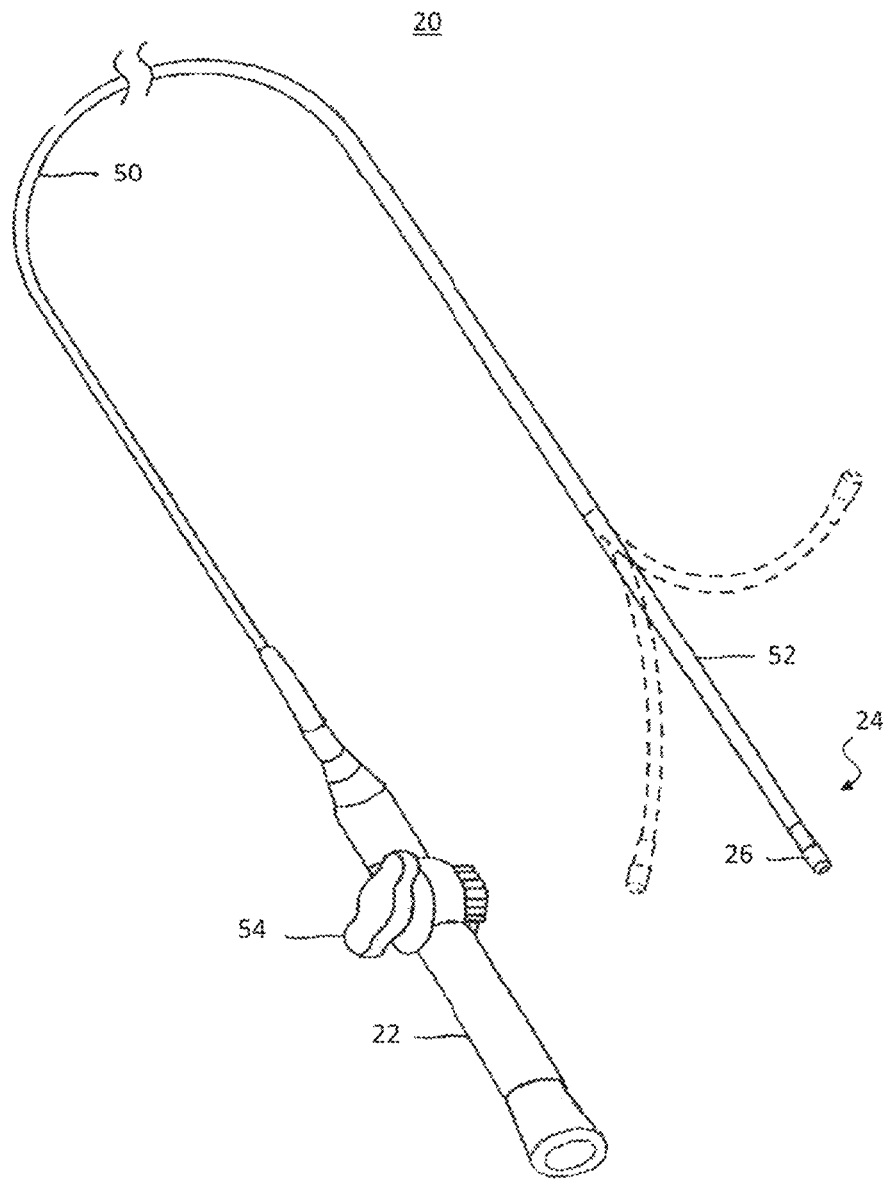
FIG. 2 is a perspective view of a catheter in accordance with an embodiment of the present invention.

A schematic elevational view of catheter 20 is illustrated in FIG. 2, showing an elongated body that includes an insertion shaft or catheter body 50 having a longitudinal axis, and an intermediate section 52 distal of the catheter body that optionally may be uni- or bi-directionally deflectable off-axis from the catheter body as indicated. Proximal of catheter body 50 is control handle 22 that allows an operator to maneuver the catheter as disclosed above, such as by deflecting intermediate section 52 when a steerable embodiment is employed. For example, control handle 22 may include deflection knob 54 that is pivoted in a clockwise or counterclockwise direction for deflection in the respective direction. In other embodiments, other steerable designs may be employed, such as the control handles for manipulating multiple control wires as described, for example, in U.S. Pat. Nos. 6,468,260, 6,500,167, 6,522,933 and 8,617,087, the entire disclosures of which are incorporated herein by reference.

Catheter body 50 is flexible, i.e., bendable, but substantially non-compressible along its length and may be of any suitable construction and made of any suitable material. In one aspect, an outer wall made of polyurethane or PEBAX may have an imbedded braided mesh of stainless steel or the like, as is generally known in the art, to increase torsional stiffness of catheter body 50 so that, when the control handle 22 is rotated, the intermediate section 52 will rotate in a corresponding manner Depending upon the intended use, the outer diameter of catheter body 50 may be approximately 8 french, and in some embodiments, may be 7 french. Likewise, the thickness of the outer wall of catheter body 50 may be thin enough so that a central lumen may accommodate any desired wires, cables and/or tubes, as will be described in further detail below. The useful length of the catheter, i.e., that portion that can be inserted into the body may vary as desired. In exemplary embodiments, the useful length may range from about 110 cm to about 120 cm. The length of the intermediate section 52 may correspond to a relatively small portion of the useful length, such as from about 3.5 cm to about 10 cm, and in some embodiments, from about 5 cm to about 6.5 cm.

Figure 3A:
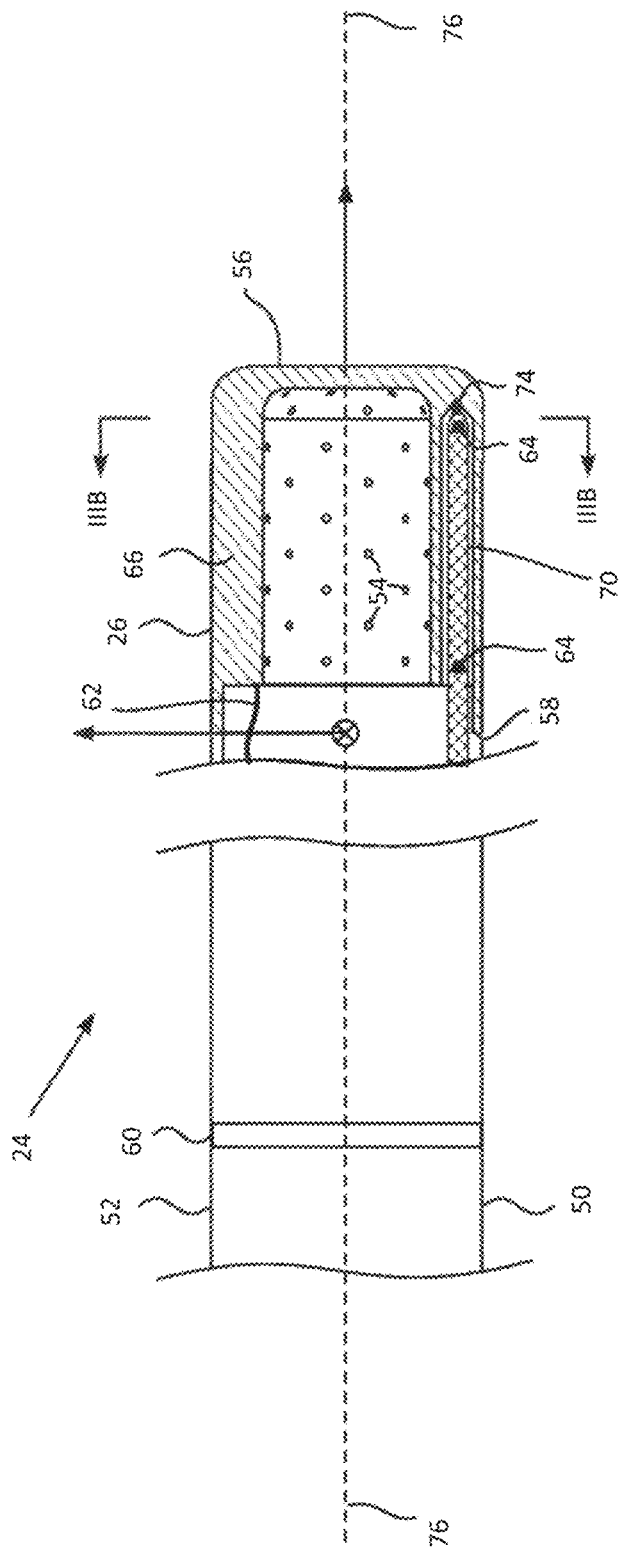
FIGS. 3A, B and C schematically illustrate a distal end of the catheter of FIG. 1 showing a tip shell electrode with position-controlled thermocouples in accordance with an embodiment of the present invention.

Details regarding one embodiment of the distal end 24 of catheter 20 are illustrated in FIGS. 3A, B and C. As indicated, electrode 26 is configured as an elongated, generally cylindrical portion with an atraumatic distal portion. The shell of electrode 26 defines an interior cavity that is in fluid communication with a lumen extending the length of catheter body 50 to supply irrigation fluid. A plurality of irrigation apertures 54 are distributed substantially evenly across the surface of electrode 26, through which fluid may exit to outside of the electrode 26, to provide cooling of electrode 26 and the environment adjacent electrode 26 as desired. The shell of electrode 26 may be made of any suitable electrically-conductive material, such as palladium, platinum, gold, iridium and combinations and alloys thereof, including, Pd/Pt (e.g., 80% Palladium/20% Platinum) and Pt/Ir (e.g., 90% Platinum/10% Iridium).

Figure 3C:
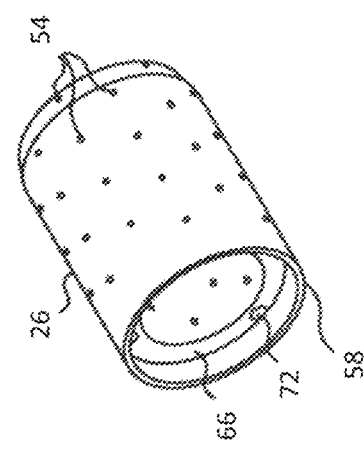
Figure 3B:
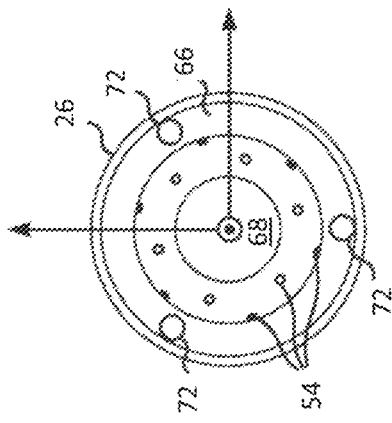

In particular, FIG. 3A is a sectional view along the length of the probe, FIG. 3B is a cross-sectional view along a cut IIIB-IIIB that is marked in FIG. 3A, and FIG. 3C is a perspective view of a section of the distal end. As shown, electrode 26 is positioned distal to intermediate section 52 of the catheter body. Tip electrode 26 may have an approximately planar conducting surface 56 at its distal end and a substantially columnar surface 58 positioned proximally. As desired, additional electrodes, such as electrode 60, may be configured as a ring electrode and may be positioned on intermediate section 52. An electrical conductor 62 conveys radio-frequency (RF) electrical energy from ablation module 44 (FIG. 1), through catheter body 50, to electrode 26, and thus energizes the electrode to ablate myocardial tissue with which the electrode is in contact. Module 44 controls the level of RF power dissipated via electrode 26. During the ablation procedure, cooling fluid flowing out through apertures 54 may irrigate the tissue under treatment.

Temperature sensors 64, typically comprising thermocouples which may be copper-constantan thermocouples for example, and thus may also be referred to herein as thermocouples 64, are mounted within tip electrode 26 at locations that are arrayed around the distal tip of the catheter, both axially and circumferentially. This example contains six sensors, with one group of three sensors in a distal location, close to the tip, and another group of three sensors in a slightly more proximal location. This distribution is shown only by way of example, however, and greater or smaller numbers of sensors may be mounted in any suitable locations within the tip electrode 26. Thermocouples 64 are connected by leads (not shown in these views) running through the length of catheter body 50 to provide temperature signals to temperature module 42.

In the disclosed embodiment, tip electrode 26 features a side wall 66 that is relatively thick, on the order of 0.5 mm thick, in order to provide the desired thermal insulation between temperature sensors 64 and the cooling fluid inside a central cavity 68 of the tip. The cooling fluid exits cavity 68 through apertures 54 as noted above. Again, with respect to this embodiment only, sensors 64 are grouped as pairs of proximal and distal thermocouples within three separate position-controlled positioning inserts 70, which are fitted into longitudinal bores 72 in side wall 66. As described in further detail below, positioning inserts 70 may be configured to positionally control the position of sensors 64 within longitudinal bores 72. Notably, positioning insert 70 may locate the sensors 64 proximally and distally, as well as towards the outer surface of electrode 26, such as surfaces 56 and/or 58. Once deployed within longitudinal bores 72, positioning inserts 70 may be held in place by potting with a suitable cement, such as epoxy, which desirably may be thermally conductive and electrically insulating. For example, epoxy resins doped with thermally conductive fillers (40-80% fill by weight), such as silver nitrate and others as described below, may be utilized to provide a high heat transfer adhesive with heat transfer coefficients in the range of 3.5-10 W/m*K. Epoxies have desirable characteristics, including low temperature cure profile, good compliance, low outgassing and good thermal stability at elevated temperatures, while readily accepting fillers. The thermal conductivity of the epoxy is influenced by the type of filler, the percentage of filler loading, and size/shape of the filler particle; all of which may have a role in the overall viscosity/rheology of the epoxy formulation. Some exemplary filler materials that may be utilized to provide thermal conductivity and electrical isolation include alumina-36 W/m*K, boron nitride-60 W/m*K, aluminum nitride-285 W/m*K and diamond 2000 W/m*K. The incorporation of filler particles into an adhesive may increase thermal conductivity and lower the thermal expansion coefficient of the adhesive. Given that increasing filler loadings may result in a higher viscosity that is more difficult to fill small bore tubing due to capillary action of the adhesive, the relative benefits may be balanced and adjusted as warranted. In other embodiments, a UV curing adhesive may be also utilized to rapidly cure the adhesive even with filler particle ranges in the 50-70% (by weight) range, particularly due to the relative small volume of thermally conductive material 82 needed to seal the ends of tubular element 80 (for example, on the order of 0.0092-0.0139 $mm^3$.) Alternative UV adhesives such as acrylated urethanes with shadow or secondary heat cures may be also mixed with thermally conductive fillers to provide an acceptable heat transfer adhesive for securing positioning inserts 70 within tip electrode 26.

The arrangement described above provides an array of six sensors 64, but other arrangements, and use of other numbers of sensors, may be employed as desired as will be apparent to those having ordinary skill in the art. All such arrangements and numbers are included within the scope of the present disclosure. Desirably, temperature sensors 64 may be positioned at different locations to measure temperature at the corresponding outer surfaces of electrode 26. Sensors 64 may be in proximity to and thermal communication with the outer surfaces, for example due to the positional control provided by positioning insert 70, and may be thermally insulated from, rather than immersed in, the cooling irrigation fluid delivered from cavity 68 through apertures 54. The sensors thus provide multiple temperature readings that are substantially independent of the cooling fluid temperature, at different locations on tip electrode 26. The sensor that gives the highest temperature reading may be the one that is in contact with the tissue being ablated, and the temperature measured by this sensor varies linearly with the actual tissue temperature. Flow of the irrigation fluid may be generally lower in areas that are in firm contact with the tissue, and the sensors in these areas typically give the highest temperature readings. In some applications, the reading from the "hottest" sensor may thus be used in particular to monitor the tissue temperature and control the applied power and duration of the ablation procedure in order to obtain the desired therapeutic result without excessive tissue damage. Alternatively or additionally, the temperature readings of the multiple sensors can be combined and interpolated to give a map of temperature over the area of the catheter tip.

In the description herein, distal end 24 is assumed to define a set of xyz orthogonal axes, where an axis 76 of the distal end corresponds to the z axis of the set. For simplicity and by way of example, the y axis is assumed to be in the plane of the paper, the xy plane is herein assumed to correspond to the plane orthogonal to the z axis, and the origin of the xyz axes is assumed to be the center catheter body 50. In one aspect, the control of positioning insert 70 may generally be with respect to the relative location of the sensors 64 in the xy plane and perpendicular to axis 76, effectively in the direction of the nearest outer surface of tip electrode 26.

Figure 4:
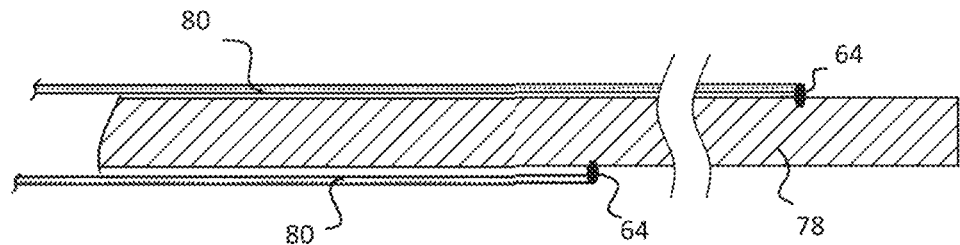
FIG. 4 is a schematic view of a plurality of thermocouples for deployment by a positioning insert in accordance with an embodiment of the present invention.

As noted, thermocouples 64 may comprise any suitable type of temperature sensor. The description that follows refers mainly to Type T, copper-constantan (Cu—Co) sensors, but any other suitable thermocouple type or other sensor construction may be used alternatively. A schematic depiction of one embodiment is shown in FIG. 4, with each thermocouple 64 formed at the junction of a copper (cu) conductor and a constantan (co) conductor. The electrical potential developing at this junction is indicative of the junction temperature. Processor 30 typically senses the temperature of a given thermocouple by sensing the electrical potential of the thermocouple junction. To simplify the wiring, one of the conductors may be shared by two or more of thermocouples 64, although this is not mandatory. For example, conductor 78 may be a 40-gauge copper conductor that is common to multiple thermocouples 64 as shown, while conductors 80 may be 48-gauge constantan conductors, with individual conductors dedicated to each thermocouple 64. Alternatively, the common conductor may be constantan and the individual conductors may be copper. In this configuration, for N thermocouples, the number of conductors that need to be routed through catheter 20 to console 32 is only N+1 (instead of 2N). This technique simplifies the catheter wiring, enables reduction in catheter diameter, and/or frees internal volume in the catheter and within electrode 26 for other purposes. Although not shown in the interests of clarity, conductors 78 and 80 typically are electrically insulated from each other except at the junctions corresponding to thermocouples 64, which may be formed by removing the insulation, such as by laser stripping and soldering or mechanically twisting the conductors together.

Typically, distal end 24 of catheter 20 contains other functional components, which are omitted for the sake of simplicity. For example, the distal end of the catheter may contain sensors of other types, such as a position sensor and a force sensor. Catheters containing components of these kinds are described, for example, in U.S. Pat. No. 8,437,832 and U.S. Patent Publication No. 2011/0130648, which are incorporated herein by reference. Thus, although positioning inserts 70 are described in the context of controlling the deployment of thermocouples 64 within electrode 26, it will be appreciated that these techniques may be extended to any of these or other components that may be carried within electrode 26.

Figure 5:
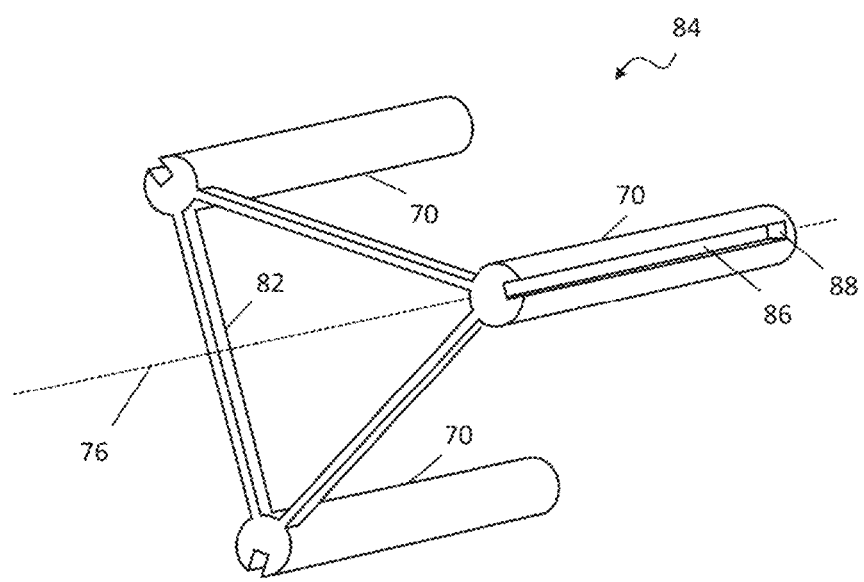
FIG. 5 is a schematic, elevational view of a positioning cartridge having a plurality of positioning inserts in accordance with an embodiment of the present invention.

As discussed above, positioning inserts 70 may be disposed within each longitudinal bore 72, with each deploying one or more thermocouples 64. Accordingly, the positioning of each thermocouple relative to the longitudinal bore 72 may be controlled. However, tip electrode 26 may comprise a plurality of bores, with thermocouples 64 deployed in each. As discussed above, this forms an array of temperature sensors and it is desirable to control the position of each relative to the other temperature sensors as well as with respect to the electrode 26 itself. To that end, rather than individually placing each positioning insert 70 within its respective longitudinal bore 72 during manufacture, a plurality of positioning inserts 70 are secured together at their proximal ends in a defined orientation by scaffold 82 to form positioning cartridge 84 as schematically shown in FIG. 5. Scaffold 82 may be formed from a suitable polymeric material having appropriate mechanical and chemical resistance properties with good temperature tolerance, such as polyether ether ketone (PEEK) or polypropylene, but any other suitable polymer including thermoplastics may be used. In one aspect, positioning cartridge 84, including positioning inserts 70 and scaffold 82 may be molded as a monolithic element. Scaffold 82 places positioning inserts 70 in a defined orientation with respect to each other that corresponds to longitudinal bores 72 in tip electrode 26. As such, in the context of this embodiment, the distal ends of positioning inserts 70 may be generally coplanar and perpendicular to longitudinal axis 76, while the positioning inserts themselves may be generally planar. In other embodiments, the spacing, orientation and relative location of positioning inserts 70 may be dictated by the characteristics of the longitudinal bores into which they are intended to be deployed.

Figure 6:
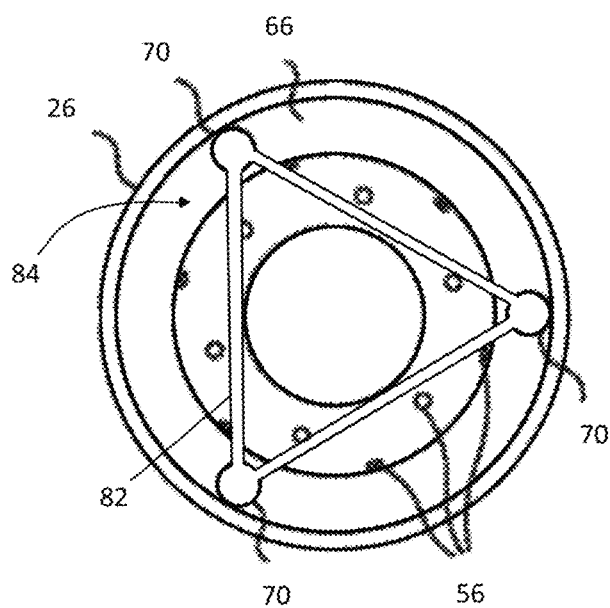
FIG. 6 is a schematic, end view of a positioning cartridge deployed within an electrode in accordance with an embodiment of the present invention.
Figure 7:
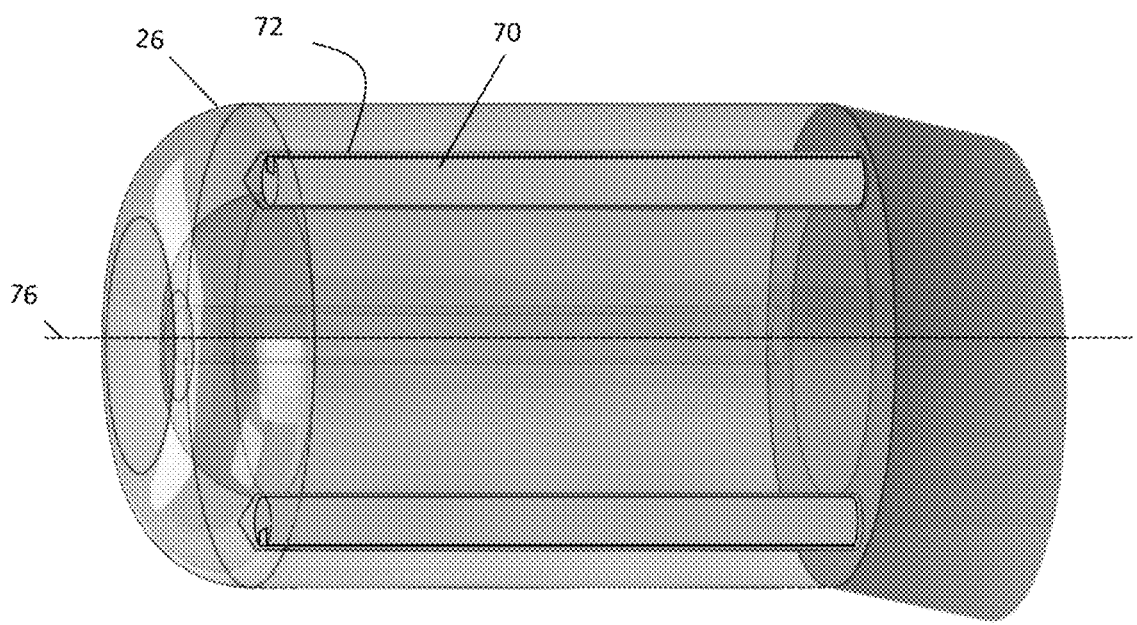
FIG. 7 is a schematic, partially transparent view of positioning inserts deployed within the longitudinal bores of an electrode in accordance with an embodiment of the present invention.

In the depicted embodiment, three positioning inserts 70 are provided, intended for use with a tip electrode 26 having three longitudinal bores 72, but in other applications, any plurality of positioning inserts 70 may be employed as warranted, such as two, four, five or more. Accordingly, scaffold 82 may be configured to hold positioning inserts 70 in a desired orientation to match the geometry of the longitudinal bores 72 into which positioning inserts 70 will be deployed. To help illustrate these aspects, FIG. 6 schematically depicts positioning cartridge 84 deployed within tip electrode 26 during manufacture in a view similar to FIG. 3B. Once positioning inserts 70 are fully deposited within longitudinal bores and secured, such as with a suitable epoxy as described above, scaffold 82 may be cut away or broken free, leaving only positioning inserts 70. This final configuration is schematically shown in the partially transparent elevational view of FIG. 7.

Additionally, as shown more clearly in FIG. 5, each positioning insert 70 features slot 86 configured to receive the conductors used to form the thermocouples (not shown for the sake of clarity). Although slot 86 is open at its proximal end to allow the conductors to extend from the thermocouples, through catheter 20 for connection to console 32, the distal end 88 may be closed to form a stop against which the thermocouple assembly may abut to facilitate a reproducible positioning of the thermocouples longitudinally within slot 86. Slot 86 also functions to cause positioning insert 70 to locate thermocouples 64 axially within longitudinal bore 72. For example, positioning inserts 70 may be sized to closely fit within the bores, so that slot 86 substantially directly opposes the outer surface of tip electrode 26. In one aspect, this may correspond to the slots 86 being oriented at an outermost radius of the positioning cartridge 84, with respect to longitudinal axis 76. As will be appreciated, this causes thermocouples 64 to be positioned relatively closely to, or even in contact with, the inner surface of the bores, minimizing or preventing the formation of an air gap that would reduce the thermal response time of sensors 64. This configuration may also be seen to minimize or otherwise reduce the distance between thermocouples 64 and the outer surface 58 or 56 of tip electrode 26, again to improve thermal response time. Still further, positioning inserts 70 may also serve as thermal insulation to reduce the influence of the cooling irrigation fluid that may be delivered through cavity 68.

Figure 8:
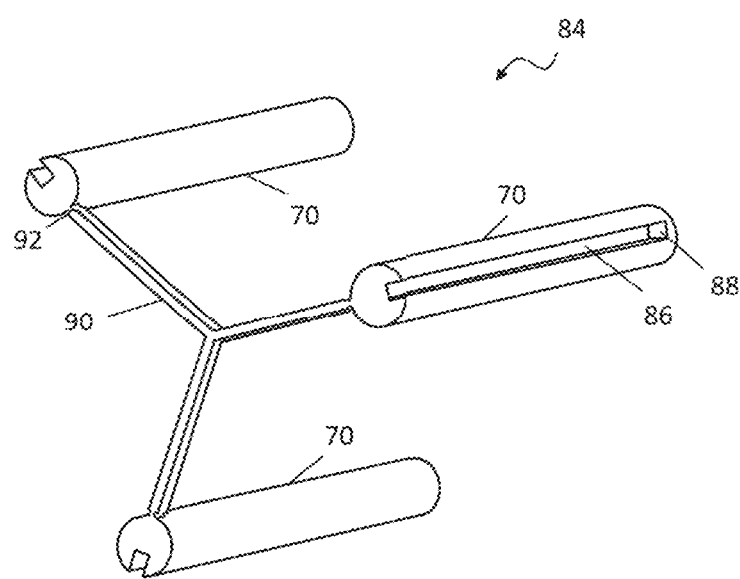
FIG. 8 is a schematic view of an alternate configuration of a positioning cartridge in accordance with an embodiment of the present invention.

It will also be appreciated that a variety of scaffold shapes may be used, so that the positioning cartridge holds positioning inserts 70 in a defined orientation with respect to each other for deployment within an electrode during manufacture. Thus, while scaffold 82 as shown in FIG. 5 generally includes a plurality of arms secured to each positioning insert 70 so that each arm joins two positioning inserts 70, any other suitable configuration may be employed. For illustration only, and without limitation, another possible configuration is shown in FIG. 8, in which scaffold 90 has a plurality of arms that extend radially from a central hub to each positioning insert 70. In this embodiment, scaffold 90 may also feature frangible junctions 92 adjacent each positioning inserts 70 to facilitate removal of scaffold 90 after positioning cartridge 84 has been used to deploy positioning inserts 70 within the longitudinal bores of an electrode during manufacture. Further, both the embodiments shown in FIGS. 5 and 8 may be seen to be configured for use in a generally cylindrical, symmetrical electrode, such as tip electrode 26. In other embodiments, the positioning cartridge may be configured to place positioning inserts 70 into any desired orientation with respect to each other so as to correspond to the characteristics of the longitudinal bores of the electrode being manufactured.

From the above, it will be appreciated that the positioning inserts 70 of positioning cartridge 84 locates proximal and distal sensors 64 in close proximity or contact with the outer shell of electrode 26. As will be appreciated, the techniques of this disclosure help more accurately measure tissue temperature adjacent electrode 26 at the areas corresponding to the positions of sensors 64. Accordingly, sensors 64 may more accurately reflect ablation conditions, for example, while exhibiting improved time response. This design also helps reduce the effect of the thermal gradient that may exist caused by the relatively hot side opposing the outer surface of electrode 26 and the relatively cool side opposing cavity 68 when filled with irrigation fluid. Effectively, positioning inserts 70 bias sensors 64 within longitudinal bore 72 towards the outer surface of electrode 26 and away from cavity 68. In conventional assemblies that do not feature the techniques of this disclosure, there may be variability in the relative axial (and longitudinal) position of the sensors between different manufactured units. Moreover, by holding positioning inserts 70 in a defined orientation as they are deployed and then secured within tip electrode 26, the use of positioning cartridge 84 represents a more reliable and reproducible technique for controlling the position of sensors 64 within longitudinal bore 72, both axially and longitudinally, and with respect to each other to form a sensing array.

As will also be appreciated, the positioning cartridges of this disclosure allow sensors 64 to be positioned at different locations within the electrode as desired and depending on the intended application. Importantly, the sensors may be reproducibly located at those desired positions. Reproducibility is desirable, as a position shift of as little as 0.001 inches may significantly alter the temperature response. Further, the relative longitudinal location of sensors 64 may be tailored as warranted. For example, a distal sensor may be oriented parallel with axis 76, towards surface 56 of electrode 26, and may provide a good representation of tissue temperature during a spot ablation on the myocardial wall, for example, while a proximal sensor may be oriented towards surface 58, generally perpendicularly to axis 76, and may provide a good representation of tissue temperature during radial ablation, such as around the ostium of a heart vessel. Yet other applications may involve 45° ablations, and the positioner may be configured to orient a sensor in that direction.

Thus, according to the techniques of this disclosure, positioning cartridge facilitates the manufacture of an electrode that provides improved temperature response and accuracy, which are important characteristics in completing a successful procedure. For example, procedures known as temperature guided ablation (TGA) involve situations very high power and short duration times, making thermal response a critical characteristic. These techniques also allow for accurate and consistent placement of the thermocouple junctions forming sensors 64, leading to repeatable and reproducible temperature response results. In comparison, conventional techniques do not provide for consistent placement of the sensors relative to the tip electrode or with respect to each other, and such catheters suffer from a lack of consistency between units as a result. Moreover, the temperature response of the catheter may not be representative of the tissue temperature during ablation due to suboptimal thermal conductivity and the potential of incorrect placement of the thermocouple junctions within the tip shell. In particular, sensors that are not deployed with a positioning cartridge have a variability relative to the bore surfaces or other recess of the electrode that lead to a propensity for wide variation of sensor orientation with respect to the tip shell. Further, conventional designs that do not adequately isolate the thermocouple junctions from the irrigation fluid and related components exhibit a thermoelectric effect extending across the bore. Temperature differences, or gradients, may influence and average the thermocouple readings when the sensors are inadequately thermally isolated. Without the control provided by positioning cartridge 84, conventional techniques are susceptible to variations during manufacture, which again can result in variability of positioning of the sensors. These differences in positioning may also lead to different distributions of the volume that is filed with epoxy, again affecting reproducibility, as different thermal responses may be created. Accordingly, the techniques of this disclosure may facilitate deployment of thermocouples and other components within the electrode, reducing the need for more costly materials or complex tooling. Similarly, the positioning cartridge may be seen to allow the consistent orientation of such components within the electrode, reducing the need for quality assurance or other validation during the manufacturing process and improving the economics.

Described herein are certain exemplary embodiments. However, one skilled in the art that pertains to the present embodiments will understand that the principles of this disclosure can be extended easily with appropriate modifications to other applications.

What is claimed is:

1. A positioning cartridge for use during manufacture of an electrode, comprising a plurality of positioning inserts, each having proximal and distal ends, at least one associated temperature sensor and a scaffold secured to the proximal end of each positioning insert, wherein the scaffold is configured to place the positioning inserts in a defined orientation with respect to each other that corresponds to a plurality of longitudinal bores of the electrode, each positioning insert comprising a longitudinal slot oriented at an outermost radius of the positioning insert for receiving the at least one associated temperature sensor.

2. The positioning cartridge of claim 1, wherein the scaffold comprises at least one arm.

3. The positioning cartridge of claim 2, wherein the positioning cartridge comprises two positioning inserts and wherein the at least one arm is secured to each positioning insert.

4. The positioning cartridge of claim 2, wherein the scaffold comprises at least one arm and wherein each arm is secured to at least one of the positioning inserts.

5. The positioning cartridge of claim 4, wherein each arm is secured to at least two of the positioning inserts.

6. The positioning cartridge of claim 1, wherein each longitudinal slot comprises a distal stop.

7. The positioning cartridge of claim 1, further comprising at least two temperature sensors disposed within each longitudinal slot.

8. The positioning cartridge of claim 1, wherein the positioning cartridge is molded as a monolithic element.

9. The positioning cartridge of claim 1, wherein the scaffold further comprises a frangible junction adjacent each of the positioning inserts.

10. A method for manufacturing an electrode, comprising:
providing the electrode, wherein the electrode comprises a plurality of longitudinal bores;
providing a positioning cartridge having a plurality of positioning inserts secured by a scaffold that holds the positioning inserts in a defined orientation with respect to each other corresponding to the longitudinal bores of the electrode;
deploying the positioning cartridge within the electrode so that each positioning insert is disposed within a longitudinal bore; and
removing the scaffold while leaving a positioning insert disposed within each longitudinal bore.

11. The method of claim 10, wherein the positioning cartridge comprises a plurality of components, such that at least one component is associated with each positioning insert.

12. The method of claim 11, wherein the plurality of components comprise temperature sensors.

13. The method of claim 12, wherein the positioning cartridge is configured to position each temperature sensor at a location adjacent an outer surface of the electrode.

* * * * *